United States Patent [19]

Spears et al.

[11] Patent Number: 5,494,796
[45] Date of Patent: Feb. 27, 1996

[54] DETECTION AND IDENTIFICATION OF MYCOBACTERIA

[75] Inventors: Patricia A. Spears; Michael C. Little, both of Raleigh, N.C.; Daryl D. Shank, Bel Air, Md.

[73] Assignee: Becton Dickinson and Company, Franklin Lakes, N.J.

[21] Appl. No.: 275,225

[22] Filed: Jul. 14, 1994

Related U.S. Application Data

[63] Continuation-in-part of Ser. No. 45,271, Apr. 5, 1993, abandoned.
[51] Int. Cl.$^6$ ............................ C12Q 1/68; C12P 19/34; C07H 21/04
[52] U.S. Cl. .......................... 435/6; 435/91.2; 536/24.32; 536/24.33
[58] Field of Search ............................ 435/6, 91.2, 91.1, 435/91.52; 536/24.32, 24.33

[56] References Cited

U.S. PATENT DOCUMENTS

| | | | |
|---|---|---|---|
| 5,270,184 | 12/1993 | Walker et al. | 435/91.2 |
| 5,314,801 | 5/1994 | Nycz et al. | 435/6 |
| 5,352,580 | 10/1994 | Spears et al. | 435/6 |

FOREIGN PATENT DOCUMENTS

| | | |
|---|---|---|
| 497272 | 8/1992 | European Pat. Off. . |
| 543612 | 5/1993 | European Pat. Off. . |
| 585660 | 3/1994 | European Pat. Off. . |

OTHER PUBLICATIONS

Walker et al., *Nucleic Acids Res.* 20(7), 1691–1696 (1992).
Walker et al., *PNAS*, 89, 392–396 (1992).
Takewaki et al., *J. Clin. Microbiol.* 31(2), 446–450 (1993).
P. W. M. Hermans, et al. "Specific Detection of Mycobacterium tuberculosis Complex Strains by Polymerase Chain Reaction" *J. Clin. Microbiol.* 28, 1204–1213 (1990).
B. Boddinghaus, et al., "Detection and Identification of Mycobacteria by Amplification of rRNA" *J. Clin. Microbiol.* 28, 1751–1759 (1990).
J. W. Fries, et al. "Genus— and species–specific DNA probes to identify mycobacteria using the polymerase chain reaction" *Mol. Cell Probes* 4, 87–105 (1990) (abstract).
R. J. Garsia, et al. "Homology of the 70–kilodalton Antigens from Mycobacterium leprae and Mycobacterium bovis with the Mycobacterium tuberculosis 71–kilodalton Antigen and with the Conserved Heat Shock Protein 70 of Eucaryotes" *Infec. Immun.* 57, 204–212 (1989).
K. R. McKenzie, et al. "Sequence and Immunogenicity of the 70–kDa Heat Shock Protein of Mycobacterium leprae" *J. Immunol.* 147, 312–319 (1991).
R. S. Gupta, et al. "Cloning of the HSP70 Gene from Halobacterium marismortui: Relatedness of Archaebacterial HSP70 to its Eubacterial Homologs and a Model for the Evolution of the HSP70 Gene" *J. Bacteriol.* 174, 4594–4605 (1992).
K. Stevenson, et al. "Complete nucleotide sequence of a gene encoding the 70 kd heat shock protein of Mycobacterium paratuberculosis" *Nucl. Acids Res.* 19, 4552 (1991).
R. B. Lathigra, et al. "A gene from Mycobacterium tuberculosis which is homologous to the DnaJ heat shock protein of *E. coli*" *Nucl. Acids Res.* 16, 1636 (1988).

*Primary Examiner*—W. Gary Jones
*Assistant Examiner*—Kenneth R. Horlick
*Attorney, Agent, or Firm*—Donna R. Fugit

[57] ABSTRACT

Genus- and species-specific oligonucleotide probes derived from the *M. paratuberculosis* 70 kD heat shock protein gene sequence. The probes are useful for detecting Mycobacteria and for identifying specific species of Mycobacteria.

22 Claims, No Drawings

DETECTION AND IDENTIFICATION OF MYCOBACTERIA

This application is a continuation-in-part of U.S. patent application Ser. No. 08/045,271, filed Apr. 5, 1993, now abandoned.

FIELD OF THE INVENTION

The Mycobacteria are a genus of bacteria which are acid-fast, non-motile, gram-positive rods. The genus comprises several species which include, but are not limited to, *Mycobacterium africanum, M. avium, M. bovis, M. bovis-BCG, M. chelonae, M. fortuitum, M. gordonae, M. intracellulare, M. kansasii, M. microti, M. scrofulaceum, M. paratuberculosis* and *M. tuberculosis*. Certain of these organisms are the causative agents of disease. For the first time since 1953, cases of mycobacterial infections are increasing in the United States. Of particular concern is tuberculosis, the etiological agent of which is *M. tuberculosis*. Many of these new cases are related to the AIDS epidemic, which provides an immune compromised population which is particularly susceptible to infection by Mycobacteria. Other mycobacterial infections are also increasing as a result of the increase in available immune compromised patients. *Mycobacterium avium, Mycobacterium kansasii* and other non-tuberculosis mycobacteria are found as opportunistic pathogens in HIV infected and other immune compromised patients.

At the present time the diagnosis of mycobacterial infections is dependent on acid-fast staining and cultivation of the organism, followed by biochemical assays. These procedures are time-consuming, and a typical diagnosis using conventional culture methods can take as long as six weeks. Automated culturing systems such as the BACTEC™ system (Becton Dickinson Microbiology Systems, Sparks, Md.) can decrease the time for diagnosis to one to two weeks. However, there is still a need to reduce the time required for diagnosing Mycobacterial infections to less than a week, preferably to about one day. Oligonucleotide probe based assays such as Southern hybridizations or dot blots are capable of returning a rapid result (i.e., in one day or less) but for diagnosis of Mycobacterial infections such methods would require an oligonucleotide probe which is specific for the genus of Mycobacteria or specific for a particular mycobacterial species if specific identification of the organism is desired. Probes of the required specificity have not previously been available for the gene encoding the 70K heat shock protein.

Heat shock proteins are a family of proteins which are expressed in elevated amounts when an organism is challenged by an increase in temperature. The heat shock proteins are highly conserved (R. J. Garcia, et al. (1989) Infection and Immunity 57:204–212; R. S. Gupta, et al. (1992) J. Bacteriology 174:4594–4605). One such heat shock protein which is highly conserved in all living cells is approximately 70 kD in size and is referred to as hsp70. The 70 kD heat shock protein has been identified in *M. tuberculosis* (R. B. Lathigra, et al. (1988) Nucleic Acids Res. 16:1636), *M. leprae* (K. R. McKenzie, et al. (1991) J. Immunol. 147:312–319) and *M. paratuberculosis* (K. Stevenson, et al. (1991) Nucleic Acids Res. 19:4552). Stevenson, et al. report a stretch of 133 amino acids (amino acids 407–540) in the *M. paratuberculosis* 70 kD heat shock protein which is 90% homologous to amino acids 131–264 of the *M. leprae* 70 kD heat shock protein and to amino acids 3–134 of the *M. tuberculosis* 71 kD heat shock protein.

One embodiment of the present invention provides oligonucleotide probes which are specific for the genus Mycobacteria and do not exhibit any cross-reactivity with closely related microorganisms such as *Rhodococcus rhodochrous* and *Nocardia asteroides*. In a second embodiment, oligonucleotide probes are provided which are specific for selected species of Mycobacteria, *R. rhodochrous* or *N. asteroides*. These probes may be used after culturing as a culture confirmation tool. Alternatively, the probes may be used prior to culturing in detection and identification methods in which the bacterial DNA is amplified. In either case, the inventive probes and diagnostic methods provide a means for rapidly discriminating between Mycobacteria-positive and Mycobacteria-negative samples, allowing the practitioner to rapidly identify a sample as negative or positive for Mycobacteria and thereby avoid the time consuming task of culturing negative samples. Species-specific probes allow rapid identification of the specific etiological agent involved in a mycobacterial infection and provide information which can be used in determining appropriate therapy in a short period of time.

SUMMARY OF THE INVENTION

The present invention provides Mycobacteria genus- and species-specific oligonucleotide probes derived from the gene encoding the *M. paratuberculosis* 70 kD heat shock protein. A 349 bp portion of the hsp70 gene was identified in eleven Mycobacteria species by polymerase chain reaction (PCR) amplification using defined primers. The amplification products were subcloned, sequenced and aligned. Similar sequence information was obtained from *R. rhodochrous* and *N. asteroides* and these sequences were also aligned to obtain probes which would not cross-react with *R. rhodochrous* or *N. asteroides*. A 204 bp segment corresponding to upstream sequences of the *M. paratuberculosis* hsp70 gene were identified in *M. avium, M. gordonae, M. tuberculosis, N. asteroides* and *R. rhodochrous* and also used to design genus-specific probes.

DETAILED DESCRIPTION OF THE INVENTION

The oligonucleotide probes of the present invention are derived from a 349 bp segment and a 204 bp segment of the *M. paratuberculosis* hsp70 gene and are useful for rapid detection of Mycobacteria by nucleic acid hybridization. The probes may either be hybridized directly to mycobacterial DNA and detected, or they may be used as primers in nucleic acid amplification reactions to produce Mycobacteria-specific amplification products which may then be detected. The probes may be of any length suitable for the particular assay format employed. In general, they are at least about 10–15 nucleotides in length. For detecting Mycobacteria they are preferably about 15–20 nucleotides in length. When used as primers in nucleic acid amplification reactions for amplification of Mycobacteria-specific target DNA, the target DNA is preferably 50–150 nucleotides in length. The probes may be either deoxyribonucleic acid (DNA) or ribonucleic acid (RNA) and may have either a naturally-occurring sugar-phosphate backbone or a backbone modified to include phosphorothioates, dithionates, alkyl phosphonates or α-nucleotides as is known in the art. The probes may be produced by chemical synthesis of the oligonucleotides, by cloning and amplification in a host cell, or by other means known in the art.

Probes according to the invention are hybridized to nucleic acid-containing samples suspected of containing Mycobacteria. The samples may comprise isolated nucleic acids or may be clinical samples. Typically, clinical samples are in the form of a biological fluid or tissue, e.g., sputum, bronchial washings, gastric washings, blood, milk, lymph, skin and soft tissues. As Mycobacteria infect both human and non-human animal species, the present invention is applicable to both human and veterinary diagnostic procedures and the sample may be obtained from either source. For example, *M. paratuberculosis* is the causative agent of Johne's disease in cattle and has been implicated in Crohn's disease in humans. *M. bovis* causes tuberculosis in cattle and is transmissible to humans. The present probes and methods may therefore be used to diagnose infection in cattle and to test cattle milk for the presence of *M. bovis* which may be transmitted to humans. Similarly, *M. avium* and *M. intracellulare* infect birds and swine, respectively, and the instant probes and methods may be used to detect such infections. In addition, humans are susceptible to infection form a variety of Mycobacteria, including *M. tuberculosis, M. kansasii, M. avium, M. intracellulare, M. scrofulaceum* and *M. fortuitum* and the instant probes and methods may be used to identify the particular species involved as an aid in determining appropriate therapy.

The oligonucleotide probes are used to detect and/or identify Mycobacteria by hybridization to mycobacterial nucleic acid. In one embodiment, the probes are used in hybridization methods for direct detection of target mycobacterial nucleic acid. These methods include Southern blots for detection of DNA, Northern blots for detection of RNA and dot blots for detection of either DNA or RNA. These methods are generally well-known in the art and are described in *Molecular Cloning: A Laboratory Manual*, 2nd ed., J. Sambrook, E. F. Fritsch and T. Maniatis, Cold Spring Harbor Laboratory Press, 1989. In a second embodiment, the presence of mycobacterial nucleic acid in a sample is detected and/or identified by genus- or species-specific amplification of target nucleic acid sequences. In this embodiment, the probes of the invention are used as primers in conventional nucleic acid amplification protocols. Any amplification protocol which relies on hybridization of primers to the target nucleic acid may be used, e.g., PCR (U.S. Pat. Nos. 4,683,195; 4,683,202; 4,800,159; 4,965,188), ligase chain reaction (LCR) (R. Weiss (1991) Science 254:1292), strand displacement amplification (SDA) (G. Walker, et al. (1992) PNAS 89:392–396; G. Walker, et al. (1992) Nucleic Acids Res. 20:1691–1696), nucleic acid based sequence amplification (NASBA) (U.S. Pat. No. 5,130,238 to Cangene), transcription based amplification (D. Kwoh, et al. (1989) PNAS 86:1173–1177), self-sustained sequence replication (J. Guatelli, et al. (1990) PNAS 87:1874–1878) or the Qβ replicase system (P. Lizardi, et al. (1988) BioTechnology 6:1197–1202). When SDA is employed, the oligonucleotide probes are preferably selected such that the GC content is low, preferably less than 70% of the total nucleotide composition of the probe. Similarly, for SDA the target sequence preferably has a low GC content to minimize secondary structure.

As nucleic acids do not require complete complementarity in order to hybridize, it is to be understood that the probe sequences herein disclosed may be modified to some extent without loss of utility as Mycobacteria genus- and species-specific probes. As is known in the art, hybridization of complementary and partially complementary nucleic acid sequences can be obtained by adjustment of the hybridization conditions to increase or decrease stringency (i.e., adjustment of hybridization temperature or salt content of the buffer). In general, sequences at least 65% homologous to the probe sequences disclosed can be used in hybridizations as Mycobacteria genus- and/or species-specific probes without significant loss of specificity.

The nucleic acid product of amplification using the inventive probes may be detected by a characteristic size, e.g., on polyacrylamide or agarose gels stained with ethidium bromide. Alternatively, mycobacterial nucleic acid in a sample or specifically amplified mycobacterial nucleic acid may be detected by hybridization to the inventive probes. For detection by hybridization the oligonucleotide probes are typically tagged with a detectable label. The detectable label is a moiety which can be detected either directly or indirectly as an indication of hybridization of the probe to the target nucleic acid. For direct detection of the label, probes may be tagged with a radioisotope and detected by autoradiography or tagged with a fluorescent moiety and detected by fluorescence as is known in the art. Alternatively, the probes may be indirectly detected by tagging with a label which requires further addition of reagents to render it detectable. Indirectly detectable labels include, for example, chemiluminescent agents, enzymes which produce visible reaction products and ligands (haptens, antibodies or antigens) which may be detected by binding to labeled specific binding partners. Particularly useful labels include biotin (detectable by binding to labeled avidin or streptavidin) and enzymes such as horseradish peroxidase or alkaline phosphatase (detectable by addition of enzyme substrates to produce colored reaction products). Methods for adding such labels to, or including such labels in, oligonucleotides are well known in the art and any of these methods are suitable for use in the present invention. For amplification reactions, the tagged detector probes may be the probes used as primers as these are incorporated into the amplification product, or at least one tagged probe different from the primers, which would be expected to hybridize to the amplification product, may be used.

For convenience, probes for genus-specific or species-specific detection of Mycobacteria may be packaged in the form of a kit which may further include other components and reagents for performing the detection methods. By way of example, such a kit contains at least one probe according to the present invention, a hybridization solution such as 6× SSC (0.9M sodium chloride, 0.09M sodium citrate, pH 7.0), 0.1M EDTA pH 8.0, 5× Denhardt's solution (0.1% w/v FICOLL TYPE 400, 0.1% w/v polyvinylpyrrolidone, 0.1% w/v bovine serum albumfin) and 100 µg/ml sheared denatured salmon sperm DNA. This hybridization buffer is commercially available from Bethesda Research Laboratories, Gaithersburg, Md. See also *Molecular Cloning: A Laboratory Manual*, supra. The components of the kit are packaged together in a common container, typically including instructions for performing a specific embodiment of the inventive methods. Additional, optional components may also be included in the kit, e.g., a second probe suitable for use with the first probe for amplification of target nucleic acid (or two pairs of probes for LCR), one or more detection probes tagged with a label, and reagents or means for performing detection of the label.

The following experimental examples are given as illustration of certain embodiments of the invention. They are not to be construed in any way as limiting the invention as defined by the appended claims.

EXAMPLES

STRAINS AND DNA PREPARATION

The Mycobacteria strains used were as follows: *M. africanum* LCDC501, *M. avium* ATCC25291, *M. bovis* CDC4, *M. bovis*-BCG CDC34, *M. chelonae* TMC1543, *M. fortuitum* TMC1529, *M. gordonae* TMC1318, *M. intracellulare* ATCC13950, *M. kansasii* TMC1201, *M. microti* LCDC203, *M. scrofulaceum* CDC78, *M. tuberculosis* ATCC27294. Non-mycobacterial microorganisms used were as follows: *Bordetella pertussis* ATCC8467, *Candida albicans* ATCC44808, *Corynebacterium diphtheriae* ATCC 119 13, *Escherichia coli* ATCC 11775, *Flavobacterium meningisepticum* ATCC 13253, *Nocardia asteroides* ATCC3308, *Rhodococcus rhodochrous* ATCC 13808, *Streptococcus pneumoniae* ATCC6303, *Acinetobacter lwoffi* ATCC19001, *Enterobacter aerogenes* ATCC13048, *Enterobacter cloacae* ATCC13047, *Haemophilus influenzae* Type B ATCC33533, *Klebsiella pneumoniae* ATCC13883, *Listeria monocytogenes* ATCC7644, *Moraxella osloensis* ATCC9281, *Morganella morganii* ATCC25830, *Neisseria lactamica* ATCC23970, *Neisseria meningitidis* ATCC13077, *Oerskovia turbata* ATCC33225, *Proteus vulgaris* ATCC13315, *Pseudomonas aerugmosa* ATCC27853, *Serratia marcescens* ATCC8100, *Shigella dysenteriae* ATCC13313, *Staphylococcus aureus* ATCC25923, *Staphylococcus epidermidis* ATCCE155, *Streptococcus pyogenes* ATCC19615, Adenovims Sigma D3390, Eukaryotic DNA from McCoy cells. The Mycobacteria strains were cultured in BACTEC vials in Middlebrook 7H9 media, then heat killed at 70° C. for 4 hours. Genomic DNA was isolated as described by S. Visuvanathan, et al. ((1989) J. Microbiol. Mtds. 10:59–64. Non-mycobacterial strains were cultured in Luria broth or other suitable media, e.g., streptococci in Todd Hewitt broth, Neisseria and Hemophilus on chocolate II agar plates and Nocardia and Rhodococcus in Actinomyces broth. Genomic DNA was isolated by the CTAB mini-prep method of F. M. Ausubel, et al. ((1987) *Current Protocols in Molecular Biology*, Greene Publishing Associates and Wiley-Interscience, New York).

NUCLEIC ACID AMPLIFICATION AND CLONING

Stevens, et al. reported a 133 amino acid sequence in the *Mycobacterium paratuberculosis* 70 kd heat shock protein which is 90% homologous among *M. paratuberculosis*, *M. tuberculosis* and *M. leprae*. This stretch of amino acids is encoded by nucleotides 1415–1814 of the gene sequence. GENBANK69 was searched with the nt 1415–1814 sequence and it showed 87% homology to the corresponding *M. tuberculosis* nucleotide sequence. Significant homology with many other 70 kD heat shock proteins from a variety of prokaryotes and eukaryotes was also found. However, the *M. leprae* nucleotide sequence was not available in GENBANK69 for comparison. Using the alignment obtained for *M. paratuberculosis* and *M. tuberculosis*, two primers were selected for use in PCR amplification. Primer PAS77 (5'-CCGTCGGTGCAGATCCAGGT-3'; SEQ ID NO:14) was derived from the sense strand of the *M. paratuberculosis* sequence from nucleotides 1415–1434. Primer PAS78 (5'-GAACTTCTCCGTCTGGTAGA-3'; SEQ ID NO:15) was derived from the antisense strand of the *M. paratuberculosis* sequence from nucleotides 1763–1744. These primers were used in a PCR amplification reaction using several mycobacterial and non-mycobacterial DNAs as templates. PCR primers were synthesized on an Applied Biosystems 380B Synthesizer as recommended by the manufacturer, deprotected at 50° C. and purified through an Oligonucleotide Purification Cartridge (Applied Biosystems, Inc.).

PCR was performed in 25–100 µl reaction volumes consisting of 10 mM Tris-HCl pH 8.3, 50 mM KCl, 1.5 mM $MgCl_2$, .001% (w/v) gelatin, 200 µM dATP, 200 µM dCTP, 200 µM dGTP, 200 µM TTP, 1.0 µM of each primer, 100 ng/100 µl of genomic DNA as template or 50 ng/100 µl plasmid DNA as template. The reactions were overlaid with mineral oil and heated to 95° C. for 5 min. 2.5 Units/100 µl of AMPLITAQ polymerase (Perkin Elmer Cetus, Norwalk, Conn.) were added and the cycling was started. The samples were typically incubated at 94° C. for 1 min. 30 sec., 37°–50° C. for 2 min., 72° C. for 3 min. for 25–30 cycles. This was followed by a 7 min. incubation at 72° C. and storage at 4° C.

There was a distinct 349 bp PCR product in all of the Mycobacteria tested, i.e., *M. africanum*, *M. avium*, *M. bovis*, *M. bovis*-BCG, *M. chelonae*, *M. fortuitum*, *M. gordonae*, *M. intracellulare*, *M. kansasii*, *M. scroulaceum* and *M. tuberculosis*. The primers showed no cross-reactivity to *E. coli*, *N. asteroides* and *R. rhodochrous*. As smaller internal oligonucleotides based on this sequence are required for nucleic acid amplification, as in SDA, it had to be determined whether there were highly conserved regions within this 349 bp product. The 349 bp amplification product (corresponding to nucleotides 1415–1763 of *M. paratuberculosis*) was subcloned and sequenced from the eleven Mycobacteria species (*M. africanum*, *M. avium*, *M. bovis*, *M. bovis*-BCG, *M. chelonae*, *M. fortuitum*, *M. gordonae*, *M. intracellulare*, *M. kansasii*, *M. scrofulaceum*, and *M. tuberculosis*). Sequencing was done using the Applied Biosystems 373A DNA sequencer using the Taq Dye Primer Cycle Sequencing Kit as recommended by the manufacturer. The sequences of the amplification products corresponding to nucleotides 1415–1763 of *M. paratuberculosis* are identified herein as SEQ ID NO:1 through SEQ ID NO:13. These sequences were aligned to design probes for genus specific detection of Mycobacteria by nucleic acid amplification and hybridization.

RHODOCOCCUS rHODOCHROUS ANALOGOUS 70K ANTIGEN SEQUENCE

To determine whether an analogous sequence existed in *Rhodococcus rhodochrous*, an *R. rhodochrous* λ-zap II library was constructed. *R. rhodochrous* genomic DNA was partially digested with Sau3AI and fragments between 0.5 and 8 kb were pooled. The fragments were then partially filled in using dGTP and dATP. The λ-zap II vector was prepared by digestion with XhoI followed by a partial fill-in using dCTP and dTTP. The *R. rhodochrous* and λ-zap II were then ligated together to form the library (CloneTech). The number of independent clones was $1.3 \times 10^6$. The library was then amplified and screened for the presence of an analogous gene encoding the 70K antigen. The library was screened with the 349 bp PCR product from *M. tuberculosis*, *M. avium*, *M. chelonae* and *M. gordonae*. Two clones were obtained which contain overlapping sequence within the 349 bp region as well as upstream and downstream sequences. The selected *R. rhodochrous* sequence (SEQ ID NO:12) was aligned with the mycobacterial sequences to design probes for hybridization to and amplification of mycobacterial nucleic acids which would not cross react with *R. rhodochrous*.

NOCARDIA aSTEROIDES ANALOGOUS 70K SEQUENCE

To determine whether an analogous sequence existed in *Nocardia asteroides*, amplification and screening were performed essentially as described for the mycobacteria. A small internal section of the 349 bp region of the 70K hsp was identified in *N. asteroides*, subcloned and sequenced. Using this sequence information an oligonucleotide having the sequence of SEQ ID NO:26 was designed as an amplification primer for SDA. This oligonucleotide corresponds to the antisense strand of the *M. paratuberculosis* sequence from nucleotide 1604–1585 with the addition of an EcoR1 site near the 5' end. The 3' end of SEQ ID NO:26 is complementary to mycobacteria target sequences and is designated "primer_bind" in the Sequence Listing. It will be understood that this mycobacteria-complementary segment (i.e., the "primer binding sequence") of SEQ ID NO:26 may also be used alone as a probe in hybridizations and with or without different 5' sequences in amplification applications other than SDA.

As will be described below, other primers of the invention have structures similar to SEQ ID NO:26, i.e., a mycobacteria-complementary primer binding sequence at the 3' end with a HincII site immediately 5' to it and additional sequences 5' to the HincII site to facilitate SDA. For each of these primers, the complementary segment is listed as "primer_bind" to identify the primer binding sequence in the SEQUENCE LISTING and to indicate its complementarity to mycobacterial nucleic acid sequences. It should be understood that the primer binding sequence of any of these primers (with or without appropriate labels) may be used alone, or with different sequences 5' to the primer binding sequence as necessary, in identification and detection applications other than SDA to obtain genus-specific or species-specific hybridization to mycobacterial nucleic acid (e.g., as PCK primers or labeled hybridization probes). As the primer binding sequence determines the specificity of the primer, any amplification primers comprising the recited primer binding sequence will have the same specificity as the oligonucleotides recited in the attached SEQUENCE LISTING.

To design an oligonucleotide upstream (5') to the region of SEQ ID NO:26, the homologies of the 70K proteins of *M. paratuberculosis* and *M. leprae* were analyzed. Based on several conserved regions (Gupta, et al.), degenerate oligonudeotides were designed. SEQ ID NO:25 is degenerate in the third position of four codons and degenerate in the second and third positions of one codon. At its 3' end SEQ ID NO:25 corresponds to the sense strand of the *M. paratuberculosis* sequence from nucleotide 1211–1230 with the addition of an EcoR1 site near the 5' end. SEQ ID NO:26 corresponds to nucleotides 1585–1604 of *M. paratuberculosis*. A product 393 bp in length was amplified from *N. asteroides* by PCR using these two oligonucleotides. This product was subcloned into the EcoR1 site of pUC18 (Pharmacia). The clones were then sequenced on an Applied Biosystems 373A DNA sequencer using the Taq Dye Primer Cycle Sequencing Kit as recommended by the manufacturer. To obtain the downstream (3') portion of the 349 bp region, oligonucleotides SEQ ID NO:27 and SEQ ID NO:28 were used in a PCR amplification reaction. SEQ ID NO:27 is the complementary oligonucleotide to SEQ ID NO:26 but does not contain an EcoR1 site at the 5' end. SEQ ID NO:28 was designed using the DNA sequence alignment of *M. paratuberculosis* and *R. rhodochrous* and corresponds to the antisense strand of the *M. paratuberculosis* sequence from nucleotide 1910–1927. This amplification therefore produced a product which slightly overlapped the sequence of the 393 bp amplification product at its 5' end and extended downstream a total of 342 bp. The 342 bp segment was subcloned into the SmaI site of pUC18. The clones were sequenced as before. The sequences of the 393 and 342 bp amplification products of *N. asteroides* were overlapped and analyzed to obtain the portion of the sequence corresponding to the 349 bp segment of *M. paratuberculosis* (SEQ ID NO: 13). SEQ ID NO:13 was aligned with the mycobacterial sequences to select non-cross reacting sequences.

ADDITIONAL UPSTREAM SEQUENCES FROM FOUR MYCOBACTERIA SPECIES

The same degenerate PCR primers used to obtain the analogous *N. asteroides* sequence described above (primers SEQ ID NO:25 and SEQ ID NO:26) were used to amplify a 204 bp product from *M. avium, M. gordonae, M. kansasii* and *M. tuberculosis*. This product was subcloned into the EcoR1 site of pUC18 (Pharmacia). The clones were sequences on an Applied Biosystems 373A sequencer using the Taq Dye Primer Cycle Sequencing Kit as recommended by the manufacturer. These sequences were aligned with each other, the previously obtained *N. asteroides* (393 bp segment) and *R. rhodochrous* sequences, and the published *M. paratuberculosis* sequence to design probes for genus-specific detection of Mycobacteria by nucleic acid amplification and hybridization. The sequences from these species correspond to nucleotides 1211–1414 of *M paratuberculosis*, with the exception of the *R. rhodochrous* sequence which corresponds to nucleotides 1265–1414. They are listed in SEQ ID NO:29, SEQ ID NO:30, SEQ ID NO:31, SEQ ID NO:32, SEQ ID NO:33 and SEQ ID NO:34.

SDA OF THE GENE ENCODING THE 70K ANTIGEN

Oligonucleotides were synthesized on an Applied Biosystems 380B Synthesizer using β cyanoethyl phosphoramidite chemistry as recommended by the manufacturer. The oligonucleotides were deprotected at 50° C. and gel purified as previously described (Ausubel, et al.)

Strand displacement amplification reactions were performed essentially as described by Walker, et al., Nuc. Acids Res. (1992), supra, in a 10–50 ml volume consisting of 6 mM $MgCl_2$, 1 mM each dGTP, dCTP, TTP and α-thio dATP, 100 μg/ml acelated bovine serum albumin, 50 mM $KPO_4$ pH 7.6, 3% (v/v) aqueous N-methyl-pyrrolidinone (NMP), 0.μM primers $S_1$ and $S_2$, 0.05 μM primers B1 and B2, 3 units/μl HincII, 0.1 unit/μl exo$^-$Klenow DNA polymerase (United States Biochemical) (Derbyshire, et al. (1988) Science 2.40:100–201) and varying amounts of target DNA. In some instances SDA reactions were performed to generate dU-substituted product. In these reactions the $MgCl_2$ concentration was 7 mM, 10% glycerol was used in lieu of NMP, and the nucleotides dUTP (0.5 mM), dGTP, dCTP and α-thio dATP (0.2 mM) were substituted. Prior to the addition of HincII and exo$^-$Klenow, the reactions were heated at 95° C. for 2 min. to denature the target DNA followed by 2 min. at 37°–40° C. to anneal the primers. Following the addition of the enzymes the reactions were incubated at 37°–40° C. for 2 hr. for amplification. Amplification was terminated by heating for 10 min. at 65° C. Product was detected by primer extension of a $^{32}$-p labeled probe and analyzed by denaturing polyacrylamide gel electrophoresis as described previously (Walker, et al.).

Probes designed by the above procedure which were directed to two regions of the 70K gene showed no cross reactivity with *N. asteroides* or *R. rhodochrous* and maintained genus specificity. These probes were tested as primers in SDA reactions using *M. tuberculosis* and *M. avium* to confirm genus-specificity. The first region was amplified with primer sets SEQ ID NO:20, SEQ ID NO:21, SEQ ID NO:22, SEQ ID NO:23 AND SEQ ID NO:24. SEQ ID NO:21, SEQ ID NO:22 and SEQ ID NO:20 are $S_1$ and $S_2$ (amplification) primers and SEQ ID NO:23 and SEQ ID NO:24 are $B_1$ and $B_2$ (bumper) primers, as defined by Walker, et al, Nucleic Acids Res., supra. Bumper primers are used in SDA to displace the extension product of the amplification primers from the target and are not necessarily target-specific. Therefore, the genus- and species-specificity of the amplification reactions in the present invention are the result of the amplification primers used and many different bumper primer pairs may be designed for use with any amplification primer pair in SDA reactions without altering the specificity.

In the present invention, the SEQ ID NO:20, SEQ ID NO:21 and SEQ ID NO:22 have complementary primer binding sequences at their 3' ends and HincII sites immediately 5' to the complementary segment. This first region includes a three base pair mismatch with SEQ ID NO:20, and a one base pair mismatch with SEQ ID NO:21/SEQ ID NO:22 between R. rhodochrous and N. asteroides respectively. Separate SDA reactions were run using SEQ ID NO:20/SEQ ID NO:21 and SEQ ID NO:20/SEQ ID NO:22 as the amplification primer pairs. Both primer pairs produced amplification products in both species of Mycobacteria tested. This region showed a sensitivity for M. avium at 10,000 molecules. There was no cross reactivity in the amplification reaction with N. asteroides or R. rhodochrous. These genus-specific probes may also be used for genus-specific detection of mycobacterial nucleic acid by hybridization as described above.

A separate region of the 70K hsp was amplified employing the probe sets SEQ ID NO: 16, SEQ ID NO:17, SEQ ID NO:18 and SEQ ID NO:19, where SEQ ID NO:17 and SEQ ID NO:18 were used as $S_1$ and $S_2$ primers and SEQ ID NO:16 and SEQ ID NO:19 were used as $B_1$ and $B_2$ primers. SEQ ID NO:17 and SEQ ID NO:18 are complementary to mycobacterial sequences at their 3' ends, as shown in the Sequence Listing, and have HincII sites immediately upstream of the primer binding sequence. The 5' ends contain additional sequences which facilitate amplification by SDA. The region defined by these probe sets amplified all ten mycobacterial species tested, i.e., M. tuberculosis, M. fortuitum, M. chelonae, M. gordonae, M. avium, M. intracellulare, M. bovis, M. kansasii, M. africanum, and M. scrofulaceum. There was no amplification in the non-mycobacterial species tested, which were N. asteroides, R. rhodochrous, Bordetella pertussis, Candida albicans, Corynebacterium diphtheriae, Escherichia coli, Flavobacterium maningisepticum, Streptococcus pneumoniae, Acmetobacter lwoffi, Enterobacter aerogenes, Enterobacter cloacae, Haemophilus influenzae type b, Klebsiella pneumoniae, Listeria monocytogenes, Moraxella osloensis, Morganella morganii, Neisseria lactamica, Neisseria meningitidis, Oerskovia turbata, Proteus vulgaris, Pseudomonas aeruginosa, Serratia marcescens, Shigella dysenteriae, Staphylococcus aureus, Staphylococcus epidermidis and Streptococcus pyogenes, and Adenovirus. The approximate sensitivity of this system is about 1,000 to 10,000 molecules of mycobacterium genomic DNA. The probes as well may be used in hybridization reactions for genus-specific detection of mycobacterial nucleic acids.

Based on the homology of the sequence alignments from nucleotides 1211–1414 of M. avium, M. gordonae, M. kansasii, M. tuberculosis and M. paratuberculosis, a conserved region was chosen for SDA amplification. Also, by aligning the previously obtained N. asteroides and R. rhodochrous sequences, primers were designed to take advantage of mismatches to eliminate cross-reactivity. The $S_1$ primer (SEQ ID NO:35) has a 3' ultimate mismatch in addition to an internal mismatch in N. asteroides and R. rhodochrous. The $S_2$ primer (SEQ ID NO:36) has a three base pair mismatch on the 3' end in N. asteroides and R. rhodochrous. Both SEQ ID NO:35 and SEQ ID NO:36 have complementary primer binding sequences at the 3' end, HincII sites, and additional 5' sequences as previously described for certain of the other probes. The sequences of both primers are identical in the five mycobacteria species tested (M. tuberculosis, M. kansasii, M. intracellulare, M. gordonae and M. avium). $B_1$ and $B_2$ primers used were SEQ ID NO:37 and SEQ ID NO:19. SDA amplification reactions were performed as described previously, and produced amplification products in all five Mycobacteria species with no cross reactivity in N. asteroides, R. rhodochrous or C. diphtheriae. The approximate sensitivity of this amplification system is 2,000 molecules of M. tuberculosis DNA.

---

What is claimed is:

1. An oligonucleotide for detecting nucleic acid of a mycobacterium selected from the group consisting of M. africanum, M. avium, M. bovis, M. bovis-BCG, M. chelonae, M. fortuitum, M. gordonae, M. intracellulare, M. kansasii, M. scrofulaceum and M. tuberculosis, the oligonucleotide having a sequence selected from the group consisting of SEQ ID NO:14 and SEQ ID NO:15.

2. An oligonucleotide for detecting nucleic acid of a mycobacterium selected from the group consisting of M. avium and M. tuberculosis, the oligonucleotide having a sequence selected from the group consisting of SEQ ID NO:20, SEQ ID NO:21 and SEQ ID NO:22.

3. An oligonucleotide for detecting nucleic acid of a mycobacterium selected from the group consisting of M. africanum, M. avium, M. bovis, M. chelonae, M. fortuitum, M. gordonae, M. intracellulare, M. kansasii, M. scrofidaceum and M. tuberculosis, the oligonucleotide having a sequence selected from the group consisting of SEQ ID NO:17 and SEQ ID NO:18.

4. An oligonucleotide for detecting nucleic acid of a mycobacterium selected from the group consisting of M. avium, M. gordonae, M. intracellulare, M. kansasii and M. tuberculosis, the oligonucleotide having a sequence selected from the group consisting of SEQ ID NO:35 and SEQ ID NO:36.

5. A method for amplifying nucleic acid of a mycobacterium selected from the group consisting of M. avium and M. tuberculosis, the method comprising the steps of:

a) hybridizing to the mycobacterial nucleic acid a pair of amplification primers, the pair of amplification primers consisting of i) a first primer comprising the primer binding sequence of SEQ ID NO:20 and a second primer comprising the primer binding sequence of SEQ ID NO:21, or ii) a third primer comprising the primer binding sequence of SEQ ID NO:20 and a fourth primer comprising the primer binding sequence of SEQ ID NO:22, and;

b) amplifying a segment of the mycobacterial nucleic acid defined by the hybridized pair of amplification primers by extending the hybridized primers on the segment of mycobacterial nucleic acid to produce an amplification product.

6. The method according to claim 5 further comprising detecting the amplification product.

7. The method according to claim 6 wherein the amplification product is detected by its size.

8. The method according to claim 6 wherein the amplification product is detected by means of a directly or indirectly detectable label.

9. The method according to claim 5 wherein the mycobacterial nucleic acid is amplified by Strand Displacement Amplification (SDA) comprising extending a pair of amplification primers consisting of SEQ ID NO:20 and SEQ ID NO:21, or SEQ ID NO:20 and SEQ ID NO:22, nicking the extended amplification primers and displacing a downstream DNA strand.

10. The method according to claim 9 further comprising hybridization and extension of bumper primers consisting of SEQ ID NO:23 and SEQ ID NO:24.

11. A method for amplifying nucleic acid of a mycobacterium selected from the group consisting of M. africanum, M. avium, M. bovis, M. chelonae, M. fortuitum, M. gordonae, M. intracelllulare, M. kansasii, M. scrofulaceum and M. tuberculosis, the method comprising the steps of:

a) hybridizing to the mycobacterial nucleic acid a pair of amplification primers consisting of a first primer comprising the primer binding sequence of SEQ ID NO:17 and a second primer comprising the primer binding sequence of SEQ ID NO:18, and;

b) amplifying a segment of the mycobacterial nucleic acid defined by the hybridized pair of amplification primers by extending the hybridized primers on the segment of mycobacterial nucleic acid to produce an amplification product.

12. The method according to claim 11 further comprising detecting the amplification product.

13. The method according to claim 12 wherein the amplification product is detected by its size.

14. The method according to claim 12 wherein the amplification product is detected by means of a directly or indirectly detectable label.

15. The method according to claim 11 wherein the mycobacterial nucleic acid is amplified by Strand Displacement Amplification (SDA) comprising extending a pair of amplification primers consisting of SEQ ID NO:17 and SEQ ID NO:18, nicking the extended amplification primers and displacing a downstream DNA strand.

16. The method according to claim 15 further comprising hybridization and extension of bumper primers consisting of SEQ ID NO:16 and SEQ ID NO:19.

17. A method for amplifying nucleic acid of a mycobacterium selected from the group consisting of *M. avium, M. gordonae, M. intracellulare, M. kansasii* and *M. tuberculosis*, the method comprising the steps of:

a) hybridizing to the mycobacterial nucleic acid a pair of amplification primers consisting of a first primer comprising the primer binding sequence of SEQ ID NO:35 and a second primer comprising the primer binding sequence of SEQ ID NO:36, and;

b) amplifying a segment of the mycobacterial nucleic acid defined by the hybridized pair of amplification primers by extending the hybridized primers on the segment of mycobacterial nucleic acid to produce an amplification product.

18. The method according to claim 17 further comprising detecting the amplification product.

19. The method according to claim 18 wherein the amplification product is detected by its size.

20. The method according to claim 18 wherein the amplification product is detected by means of a directly or indirectly detectable label.

21. The method according to claim 17 wherein the mycobacterial nucleic acid is amplified by Strand Displacement Amplification (SDA) comprising extending a pair of amplification primers consisting of SEQ ID NO:35 and SEQ ID NO:36, nicking the extended amplification primers and displacing a downstream DNA strand.

22. The method according to claim 21 further comprising hybridization and extension of bumper primers consisting of SEQ ID NO:19 and SEQ ID NO:37.

* * * * *

SEQUENCE LISTING ( 1 ) GENERAL INFORMATION:

( i i i ) NUMBER OF SEQUENCES: 37

( 2 ) INFORMATION FOR SEQ ID NO:1:

( i ) SEQUENCE CHARACTERISTICS:
        ( A ) LENGTH: 349 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Mycobacterium avium ( x i ) SEQUENCE DESCRIPTION: SEQ ID NO:1:

```
CCGTCGGTGC   AGATCCAGGT   GTACCAGGGT   GAGCGCGAAA   TCGCCGCGCA   CAACAAGCTG        60

CTCGGCTCCT   TCGAGCTGAC   CGGAATCCCG   CCGGCGCCCC   GCGGCGTGCC   GCAGATCGAG       120

GTCACCTTCG   ACATCGACGC   CAACGGCATC   GTGCACGTCA   CCGCGAAGGA   CAAGGGCACC       180

GGTAAGGAGA   ACACGATCAA   GATCCAGGAG   GGCTCCGGCC   TGTCCAAGGA   GGAGATCGAC       240

CGGATGATCA   AGGACGCCGA   GGCGCACGCC   GAGGAGGACC   GCAAGCGGCG   CGAGGAAGCC       300
```

GACGTCCGCA ACCAAGCGGA ATCGCTTGTC TACCAGACGG AGAAGTTCG          349

( 2 ) INFORMATION FOR SEQ ID NO:2:

( i ) SEQUENCE CHARACTERISTICS:
           ( A ) LENGTH: 349 base pairs
           ( B ) TYPE: nucleic acid
           ( C ) STRANDEDNESS: double
           ( D ) TOPOLOGY: linear ( i i ) MOLECULE TYPE: DNA (genomic)

( v i ) ORIGINAL SOURCE:
           ( A ) ORGANISM: Mycobacterium intracellulare ( x i ) SEQUENCE DESCRIPTION: SEQ ID NO:2:

CCGTCGGTGC AGATCCAGGT GTACCAGGGT GAGCGCGAAA TCGCTTCGCA CAACAAGCTG          60

CTCGGCTCCT TCGAGCTGAC CGGCATCCCG CCGGCGCCCC GCGGCGTCCC GCAGATCGAG          120

GTCACCTTCG ACATCGACGC CAACGGCATC GTGCACGTCA CGGCCAAGGA CAAGGGCACC          180

GGCAAGGAGA ACACGATCAA AATCCAGGAG GGCTCCGGCC TGTCCAAGGA GGAGATCGAC          240

CGGATGATCA AGGACGCCGA GGCGCACGCC GAGGAGGACC GCCAGCGTCG CGAGGAGGCC          300

GACGTCCGCA ACCAGGCCGA ATCGCTGGTC TACCAGACGG AGAAGTTCG          349

( 2 ) INFORMATION FOR SEQ ID NO:3:

( i ) SEQUENCE CHARACTERISTICS:
           ( A ) LENGTH: 349 base pairs
           ( B ) TYPE: nucleic acid
           ( C ) STRANDEDNESS: double
           ( D ) TOPOLOGY: linear ( i i ) MOLECULE TYPE: DNA (genomic)

( v i ) ORIGINAL SOURCE:
           ( A ) ORGANISM: Mycobacterium scrofulaceum ( x i ) SEQUENCE DESCRIPTION: SEQ ID NO:3:

CCGTCGGTGC AGATCCAGGT CTATCAGGGT GAGCGCGAAA TCGCTTCGCA CAACAAGCTG          60

CTCGGCTCCT TCGAGCTGAC CGGCATCCCG CCGGCCCCGC GCGGCGTGCC CCAGATCGAG          120

GTCACCTTCG ACATCGACGC CAACGGCATC GTGCACGTCA CGGCCAAGGA CAAGGGCACC          180

GGCAAGGAGA ACACGATCAA GATCCAGCAG GGCTCCGGCC TGTCCAAGGA GGAGATCGAC          240

CGGATGATCA AGGACGCCGA GGCGCACGCC GAGGAGGACC GCCAGCGTCG CGAGGAGGCC          300

GACATCCGCA ACCAGGCCGA GTCGCTGGTC TACCAGACGG AGAAGTTCG          349

( 2 ) INFORMATION FOR SEQ ID NO:4:

( i ) SEQUENCE CHARACTERISTICS:
           ( A ) LENGTH: 349 base pairs
           ( B ) TYPE: nucleic acid
           ( C ) STRANDEDNESS: double
           ( D ) TOPOLOGY: linear ( i i ) MOLECULE TYPE: DNA (genomic)

( v i ) ORIGINAL SOURCE:
           ( A ) ORGANISM: Mycobacterium tuberculosis ( x i ) SEQUENCE DESCRIPTION: SEQ ID NO:4:

CCGTCGGTGC AGATCCAGGT CTATCAGGGG GAGCGTGAGA TCGCCGCGCA CAACAAGTTG          60

CTCGGGTCCT TCGAGCTGAC CGGCATCCCG CCGGCGCCGC GGGGGATTCC GCAGATCGAG          120

GTCACTTTCG ACATCGACGC CAACGGCATT GTGCACGTCA CCGCCAAGGA CAAGGGCACC          180

```
GGCAAGGAGA  ACACGATCCG  AATCCAGGAA  GGCTCGGGCC  TGTCCAAGGA  AGACATTGAC           240

CGCATGATCA  AGGACGCCGA  AGCGCACGCC  GAGGAGGATC  GCAAGCGTCG  CGAGGAGGCC           300

GATGTTCGTA  ATCAAGCCGA  GACATTGGTC  TACCAGACGG  AGAAGTTCG                        349
```

( 2 ) INFORMATION FOR SEQ ID NO:5:

( i ) SEQUENCE CHARACTERISTICS:
        ( A ) LENGTH: 349 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Mycobacterium gordonae ( x i ) SEQUENCE DESCRIPTION: SEQ ID NO:5:

```
CCGTCGGTGC  AGATCCAGGT  CTACCAGGGT  GAGCGTGAGA  TCGCCTCGGC  CAACAAGCTG            60

CTCGGCAGCT  TCGAGTTGAC  CGGTATCGCC  CCGGCTCCGC  GCGGGGTGCC  CCAGATCGAG           120

GTCACCTTTG  ACATCGACGC  CAACGGCATC  GTGCACGTCA  CGGCCAAGGA  CAAGGGCACC           180

GGCAAGGAGA  ACACGATCCG  TATCCAGGAG  GGCTCCGGCA  TCTCCAAGGA  AGAGATCGAC           240

CGGATGATCA  AGGAGGCCGA  AGCGCACGCG  GACGAGGACC  GCAAGCGTCG  CGAGGAGGCC           300

GACGTTCGCA  ACCAGGCCGA  GACGCTGGTC  TACCAGACGG  AGAAGTTCG                        349
```

( 2 ) INFORMATION FOR SEQ ID NO:6:

( i ) SEQUENCE CHARACTERISTICS:
        ( A ) LENGTH: 349 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Mycobacterium fortuitum ( x i ) SEQUENCE DESCRIPTION: SEQ ID NO:6:

```
CCGTCGGTGC  AGATCCAGGT  CTTCCAGGGT  GAGCGCGAAA  TCGCTTCTCA  CAACAAGCTG            60

CTCGGCTCCT  TCGAGCTGAC  CGGCATCCCG  CCGGCCCCGC  GTGGCGTGCC  GCAGATCGAG           120

GTCACCTTCG  ACATCGACGC  CAACGGCATC  GTGCACGTGA  CCGCCAAGGA  CAAGGGCACC           180

GGCAAGGAAA  ACACGATCAA  GATCCAGGAA  GGCTCCGGCC  TGTCCAAGGA  AGAGATCGAC           240

CGGATGATCA  AGGACGCCGA  GGCACGCACC  GAAGAGGACA  GAAGCGTCG  CGAAGAGGCC            300

GACGTCCGCA  ACCAAGCCGA  GTCGCTGGTC  TACCAGACGG  AGAAGTTCG                        349
```

( 2 ) INFORMATION FOR SEQ ID NO:7:

( i ) SEQUENCE CHARACTERISTICS:
        ( A ) LENGTH: 349 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Mycobacterium bovis- BCG ( x i ) SEQUENCE DESCRIPTION: SEQ ID NO:7:

```
CCGTCGGTGC  AGATCCAGGT  CTATCAGGGG  GAGCGTGAGA  TCGCCGCGCA  CAACAAGTTG            60
```

```
CTCGGGTCCT  TCGAGCTGAC  CGGCATCCCG  CCGGCGCCGC  GGGGGATTCC  GCAGATCGAG     120

GTCACTTTCG  ACATCGACGC  CAACGGCATT  GTGCACGTCA  CCGCCAAGGA  CAAGGGCACC     180

GGCAAGGAGA  ACACGATCCG  AATCCAGGAA  GGCTCGGGCC  TGTCCAAGGA  AGACATTGAC     240

CGCATGATCA  AGGACGCCGA  AGCGCACGCC  GAGGAGGATC  GCAAGCGTCG  CGAGGAGGCC     300

GATGTTCGTA  ATCAAGCCGA  GACATTGGTC  TACCAGACGG  AGAAGTTCG               349
```

( 2 ) INFORMATION FOR SEQ ID NO:8:

( i ) SEQUENCE CHARACTERISTICS:
        ( A ) LENGTH: 349 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Mycobacterium bovis ( x i ) SEQUENCE DESCRIPTION: SEQ ID NO:8:

```
CCGTCGGTGC  AGATCCAGGT  CTATCAGGGG  GAGCGTGAGA  TCGCCGCGCA  CAACAAGTTG     60

CTCGGGTCCT  TCGAGCTGAC  CGGCATCCCG  CCGGCGCCGC  GGGGGATTCC  GCAGATCGAG     120

GTCACTTTCG  ACATCGACGC  CAACGGCATT  GTGCACGTCA  CCGCCAAGGA  CAAGGGCACC     180

GGCAAGGAGA  ACACGATCCG  AATCCAGGAA  GGCTCGGGCC  TGTCCAAGGA  AGACATTGAC     240

CGCATGATCA  AGGACGCCGA  AGCGCACGCC  GAGGAGGATC  GCAAGCGTCG  CGAGGAGGCC     300

GATGTTCGTA  ATCAAGCCGA  GACATTGGTC  TACCAGACGG  AGAAGTTCG               349
```

( 2 ) INFORMATION FOR SEQ ID NO:9:

( i ) SEQUENCE CHARACTERISTICS:
        ( A ) LENGTH: 349 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Mycobacterium chelonae ( x i ) SEQUENCE DESCRIPTION: SEQ ID NO:9:

```
CCGTCGGTGC  AGATCCAGGT  GTATCAGGGT  GAGCGCGAAA  TCGCTTCGCA  CAACAAGCTC     60

CTGGGCTCCT  TCGAGCTGAC  CGGAATTCCG  CCGGCCCCGC  GCGGTGTGCC  GCAGATCGAG     120

GTCACCTTCG  ACATCGATGC  GAACGGCATC  GTGCACGTGA  CCGCGAAGGA  CAAGGGCACC     180

GGCAAGGAGA  ACACGATCAA  GATCCAGGAA  GGCTCCGGCC  TGTCCAAGGA  AGAGATCGAC     240

CGGGTGATCA  AGGACGCCGA  GGCGCACGCC  GACGAGGACA  AGAAGCGCCG  CGAAGAGGCC     300

GATGTCCGTA  ACCAGGCCGA  GTCGCTGGTC  TACCAGACGG  AGAAGTTCA                349
```

( 2 ) INFORMATION FOR SEQ ID NO:10:

( i ) SEQUENCE CHARACTERISTICS:
        ( A ) LENGTH: 349 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Mycobacterium kansasii ( x i ) SEQUENCE DESCRIPTION: SEQ ID NO:10:

| | | | | | |
|---|---|---|---|---|---|
| CCGTCGGTGC | AGATCCAGGT | CTATCAGGGT | GAGCGCGAGA | TCGCCTCGCA | CAACAAGCTG | 60
| CTCGGCTCCT | TCGAGCTGAC | CGGCATCCCG | CCGGCGCCCC | GCGGCGTCCC | GCAGATCGAG | 120
| GTCACCTTCG | ACATCGACGC | CAACGGCATC | GTGCATGTCA | CGGCCAAGGA | CAAGGGCACC | 180
| GGCAAGGAGA | ACACCATCCG | GATCCAGGAA | GGCTCGGGCC | TGTCCAAGGA | AGAGATCGAC | 240
| CGGATGATCA | AGGAYGCCGA | GGCGCACGCC | GAGGAGGACC | GCAAGCGTCG | CGAGGAGGCC | 300
| GACGTCCGCA | ACCAGGCCGA | GACGCTGGTC | TACCAGACGG | AGAAGTTCG | | 349

( 2 ) INFORMATION FOR SEQ ID NO:11:

( i ) SEQUENCE CHARACTERISTICS:
        ( A ) LENGTH: 349 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Mycobacterium africanum ( x i ) SEQUENCE DESCRIPTION: SEQ ID NO:11:

| | | | | | |
|---|---|---|---|---|---|
| CCGTCGGTGC | AGATCCAGGT | GTATCAGGGT | GAGCGCGAAA | TCGCCGCGCA | CAACAAGCTG | 60
| CTCGGCTCCT | TCGAGCTGAC | CGGAATCCTG | CCGGCGCCCC | GCGGCGTGCC | GCAGATCGAG | 120
| GTCACCTTCG | ACATCGACGC | CAACGGCATC | GTGCACGTCA | CCGCCAAGGA | CAAGGGCACC | 180
| GGTAAGGAGA | ACACGATCAA | GATCCAGGAG | GGCTCCGGCC | TGTCCAAGGA | AGAGATCGAC | 240
| CGGATGATCA | AGGACGCCGA | GGCGCACGCC | GAGGAGGACC | GCAAGCGGCG | CGAGGAAGCC | 300
| GACGTCCGCA | ACCAAGCGGA | ATCGCTTGTC | TACCAGACGG | AGAAGTTCG | | 349

( 2 ) INFORMATION FOR SEQ ID NO:12:

( i ) SEQUENCE CHARACTERISTICS:
        ( A ) LENGTH: 349 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Rhodococcus rhodochrous ( x i ) SEQUENCE DESCRIPTION: SEQ ID NO:12:

| | | | | | |
|---|---|---|---|---|---|
| CCGTCCGTGC | AGATCCAGGT | CTACCAGGGC | GAGCGTGAGA | TCGCGGCGCA | CAACAAGCTG | 60
| CTCGGTTCGT | TCGAGCTCGG | CGGCATCGCG | CCGGCTCCGC | GCGGTGTCCC | GCAGATCGAG | 120
| GTGGCCTTCG | GCATCGACGC | CAACGGCATC | GTCCACGTCA | CCGCCCGCGA | CAAGGGCACC | 180
| GGCAAGGAGA | ACACGATCAA | GATCCAGGAA | GGCTCCGGCC | TCTCCCAGGA | GGAGATCGAT | 240
| CGGATGGTCA | AGGACGCCGA | GGTCCACGCC | GAGGAGGACC | GCAAGCGTCG | CGAGGAGGCC | 300
| GAGGTCCGCA | ACCAGGCCGA | GTCGCTCGTG | CACCAGACCG | AGAAGTTCA | | 349

( 2 ) INFORMATION FOR SEQ ID NO:13:

( i ) SEQUENCE CHARACTERISTICS:
        ( A ) LENGTH: 349 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
    ( A ) ORGANISM: Nocardia asteroides ( x i ) SEQUENCE DESCRIPTION: SEQ ID NO:13:

| | | | | | |
|---|---|---|---|---|---|
| CCGTCGGTGC | AGATCCAGGT | CTTCCAGGGC | GAGCGCGAGA | TCGCCGCGCA | CAACAAGCTG | 60 |
| CTGGGTTCCT | TCGAGCTCAC | CGGCATCCCG | CCGGCTCCGC | GTGGCGTGCC | CCAGATCGAG | 120 |
| GTGACCTTCG | ACATCGACGC | CAACGGCATC | GTGCACGTCA | CCGCGAAGGA | CAAGGGCACC | 180 |
| GGCAAGGAGA | ACACGATCAA | GATCCAGGAC | GGCTCCGGCC | TGTCCAAGGA | AGAGATCGAC | 240 |
| CGGATGATCA | AGGACGCCGA | GCAGCACGCG | GCCGAGGACA | AGGCCCGGCG | CGAGGAGGCC | 300 |
| GAGACCCGCA | ACCAGGCCGA | GACCCTGGTG | CACCAGACCG | AGAAGTTCA | | 349 |

( 2 ) INFORMATION FOR SEQ ID NO:14:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

CCGTCGGTGC AGATCCAGGT     20

( 2 ) INFORMATION FOR SEQ ID NO:15:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

GAACTTCTCC GTCTGGTAGA     20

( 2 ) INFORMATION FOR SEQ ID NO:16:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

CTTCGAGCTG ACCG     14

( 2 ) INFORMATION FOR SEQ ID NO:17:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i x ) FEATURE:
        ( A ) NAME/KEY: primer_bind
        ( B ) LOCATION: 25..36

( x i ) SEQUENCE DESCRIPTION: SEQ ID NO:17:

TTGAATAGTC GGTTACTTGT TGACGCAGAT CGAGGT     36

( 2 ) INFORMATION FOR SEQ ID NO:18:

( i ) SEQUENCE CHARACTERISTICS:
        ( A ) LENGTH: 39 base pairs ( B ) TYPE: nucleic acid
( C ) STRANDEDNESS: single
( D ) TOPOLOGY: linear ( i x ) FEATURE:
( A ) NAME/KEY: primer_bind
( B ) LOCATION: 25..39

( x i ) SEQUENCE DESCRIPTION: SEQ ID NO:18:

TTGAAGTAAC CGACTATTGT TGACGGTGCC CTTGTCCTT 39

( 2 ) INFORMATION FOR SEQ ID NO:19:

( i ) SEQUENCE CHARACTERISTICS:
( A ) LENGTH: 13 base pairs
( B ) TYPE: nucleic acid
( C ) STRANDEDNESS: single
( D ) TOPOLOGY: linear ( x i ) SEQUENCE DESCRIPTION: SEQ ID NO:19:

TCCTTGGACA GGC 13

( 2 ) INFORMATION FOR SEQ ID NO:20:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( i x ) FEATURE:
( A ) NAME/KEY: primer_bind
( B ) LOCATION: 25..38

( x i ) SEQUENCE DESCRIPTION: SEQ ID NO:20:

TTGAATAGTC GGTTAGATGT TGACACGTCA CGGGGAAG 38

( 2 ) INFORMATION FOR SEQ ID NO:21:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( i x ) FEATURE:
( A ) NAME/KEY: primer_bind
( B ) LOCATION: 25..33

( x i ) SEQUENCE DESCRIPTION: SEQ ID NO:21:

TTGATCTAAC CGACTATTGT TGACCCGAGC CCT 33

( 2 ) INFORMATION FOR SEQ ID NO:22:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( i x ) FEATURE:
( A ) NAME/KEY: primer_bind
( B ) LOCATION: 25..33

( x i ) SEQUENCE DESCRIPTION: SEQ ID NO:22:

TTGATCTAAC CGACTATTGT TGACCGGAGC CTT 33

( 2 ) INFORMATION FOR SEQ ID NO:23:

( i ) SEQUENCE CHARACTERISTICS:

(A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO:23:

TCGGCGTCCT TGAT                                                                              14

(2) INFORMATION FOR SEQ ID NO:24:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO:24:

CAGATCGAGG TCAC                                                                              14

(2) INFORMATION FOR SEQ ID NO:25:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ix) FEATURE:
        (A) NAME/KEY: primer_bind
        (B) LOCATION: 10..29

(xi) SEQUENCE DESCRIPTION: SEQ ID NO:25:

GTGGAATTCA ACCCSGAYGA RGYYGTNGC                                                              29

(2) INFORMATION FOR SEQ ID NO:26:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ix) FEATURE:
        (A) NAME/KEY: primer_bind
        (B) LOCATION: 10..29

(xi) SEQUENCE DESCRIPTION: SEQ ID NO:26:

GTGGAATTCT CTCCTTRCCG GTGCCCTTG                                                              29

(2) INFORMATION FOR SEQ ID NO:27:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:27:

CAAGGGCACC GGCAAGGAGA                                                                        20

(2) INFORMATION FOR SEQ ID NO:28:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:28:

CCGAGGGCCT GCGACTC                                                                                  17

( 2 ) INFORMATION FOR SEQ ID NO:29:

( i ) SEQUENCE CHARACTERISTICS:
          ( A ) LENGTH: 204 base pairs
          ( B ) TYPE: nucleic acid
          ( C ) STRANDEDNESS: double
          ( D ) TOPOLOGY: linear ( i i ) MOLECULE TYPE: DNA (genomic)

( v i ) ORIGINAL SOURCE:
          ( A ) ORGANISM: Mycobacterium avium ( x i ) SEQUENCE DESCRIPTION: SEQ ID NO:29:

AACCCGGATG AGGTCGTGGC GGTGGGTGCC GCCCTGCAGG CTGGTGTGCT TAAGGGCGAG        60

GTGAAAGACG TTCTGCTGCT TGACGTTACG CCGCTGAGCC TGGGTATCGA GACCAAGGGT        120

GGCGTGATGA CCAAGCTGAT CGAACGCAAC ACCACCATCC CGACCAAGCG GTCCGAGACG        180

TTCACCACGG CCGACGACAA CCAG                                              204

( 2 ) INFORMATION FOR SEQ ID NO:30:

( i ) SEQUENCE CHARACTERISTICS:
          ( A ) LENGTH: 204 base pairs
          ( B ) TYPE: nucleic acid
          ( C ) STRANDEDNESS: double
          ( D ) TOPOLOGY: linear ( i i ) MOLECULE TYPE: DNA (genomic)

( v i ) ORIGINAL SOURCE:
          ( A ) ORGANISM: Mycobacterium gordonae ( x i ) SEQUENCE DESCRIPTION: SEQ ID NO:30:

AACCCGGATG AGGTTGTGGC CGTGGGCGCC GCGCTGCAGG CCGGTGTGCT YAAGGGCGAG        60

GTGAAAGATG TTCTGCTGCT TGACGTTACG CCGCTGAGCC TGGGTATCGA GACCAAGGGC        120

GGCGTGATGA CCAAGCTCAT CGAGCGCAAC ACCACCATCC CGACCAAGCG GTCGGAGACC        180

TTCACCACGG CCGACGACAA CCAG                                              204

( 2 ) INFORMATION FOR SEQ ID NO:31:

( i ) SEQUENCE CHARACTERISTICS:
          ( A ) LENGTH: 204 base pairs
          ( B ) TYPE: nucleic acid
          ( C ) STRANDEDNESS: double
          ( D ) TOPOLOGY: linear ( i i ) MOLECULE TYPE: DNA (genomic)

( v i ) ORIGINAL SOURCE:
          ( A ) ORGANISM: Mycobacterium kansasii ( x i ) SEQUENCE DESCRIPTION: SEQ ID NO:31:

AACCCCGACG AGGTTGTGGC CGTCGGTGCC GCGCTGCAGG CCGGTGTCCT CAAGGGCGAG        60

GTGAAAGATG TTCTGCTGCT TGATGTTACG CCGCTGAGCC TGGGTATCGA GACAAAGGGC        120

GGCGTGATGA CCAAGCTGAT CGAGCGCAAC GCCACGATCC CGACCAAGCG GTCGGAGACC        180

TTCACCACCG CCGACGACAA CCAG                                              204

( 2 ) INFORMATION FOR SEQ ID NO:32:

( i ) SEQUENCE CHARACTERISTICS:
          ( A ) LENGTH: 204 base pairs
          ( B ) TYPE: nucleic acid (C) STRANDEDNESS: double
(D) TOPOLOGY: linear (i i) MOLECULE TYPE: DNA (genomic)

(v i) ORIGINAL SOURCE:
 (A) ORGANISM: Mycobacterium tuberculosis (x i) SEQUENCE DESCRIPTION: SEQ ID NO:32:

| | | | | | | |
|---|---|---|---|---|---|---|
| AACCCGGATG | AAGTTGTAGC | GGTGGGAGCC | GCTCTGCAGG | CCGGCGTGCT | CAAGGGCGAG | 60 |
| GTGAAAGACG | TTCTGCTGCT | TGATGTTACC | CCGCTGAGCC | TGGGTATCGA | GACCAAGGGC | 120 |
| GGGGTGATGA | CCAGGCTCAT | CGAGCGCAAC | ACCACGATCC | CCACCAAGCG | GTCGGAGACT | 180 |
| TTCACCACCG | CCGACGACAA | CCAA | | | | 204 |

(2) INFORMATION FOR SEQ ID NO:33:

(i) SEQUENCE CHARACTERISTICS:
  (A) LENGTH: 204 base pairs
  (B) TYPE: nucleic acid
  (C) STRANDEDNESS: double
  (D) TOPOLOGY: linear (i i) MOLECULE TYPE: DNA (genomic)

(v i) ORIGINAL SOURCE:
  (A) ORGANISM: Nocardia asteroides (x i) SEQUENCE DESCRIPTION: SEQ ID NO:33:

| | | | | | | |
|---|---|---|---|---|---|---|
| AACCCGGACG | AGGCTGTAGC | CGTCGGCGCC | GCCCTGCAGG | CCGGTGTGCT | CAAGGGTGAG | 60 |
| GTCAAGGACG | TCCTGCTGCT | CGACGTGACC | CCGCTGTCGC | TGGGTATCGA | GACCAAGGGC | 120 |
| GGCGTGATGA | CCAAGCTCAT | CGAGCGCAAC | ACCACGATCC | CGACCAAGCG | TTCGGAGACC | 180 |
| TTCACCACCG | CCGACGACAA | CCAG | | | | 204 |

(2) INFORMATION FOR SEQ ID NO:34:

(i) SEQUENCE CHARACTERISTICS:
  (A) LENGTH: 150 base pairs
  (B) TYPE: nucleic acid
  (C) STRANDEDNESS: double
  (D) TOPOLOGY: linear (i i) MOLECULE TYPE: DNA (genomic)

(v i) ORIGINAL SOURCE:
  (A) ORGANISM: Rhodococcus rhodochrous (x i) SEQUENCE DESCRIPTION: SEQ ID NO:34:

| | | | | | | |
|---|---|---|---|---|---|---|
| GCCGAGGTCA | AGGACGTGCT | GCTGCTCGAC | GTCACCCCGC | TGTCGCTCGG | TATCGAGACC | 60 |
| AAGGGCGGCG | TGATGACCAA | GCTCATCGAG | CGCAACACCA | CGATCCCCAC | CAAGCGGTCC | 120 |
| GAGACCTTCA | CCACGGCCGA | CGACAAAAAA | | | | 150 |

(2) INFORMATION FOR SEQ ID NO:35:

(i) SEQUENCE CHARACTERISTICS:
  (A) LENGTH: 36 base pairs
  (B) TYPE: nucleic acid
  (C) STRANDEDNESS: single
  (D) TOPOLOGY: linear (i x) FEATURE:
  (A) NAME/KEY: primer_bind
  (B) LOCATION: 25..36

(x i) SEQUENCE DESCRIPTION: SEQ ID NO:35:

| | | | |
|---|---|---|---|
| TTGAATAGTC | GGTTAGAAGT | TGACAAGGGC GAGGTG | 36 |

( 2 ) INFORMATION FOR SEQ ID NO:36:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( i x ) FEATURE:
( A ) NAME/KEY: primer_bind
( B ) LOCATION: 25..38

( x i ) SEQUENCE DESCRIPTION: SEQ ID NO:36:

TTGAAGTAAC CGACTATTGT TGACTCGATA CCCAGGCT 38

( 2 ) INFORMATION FOR SEQ ID NO:37:

( i ) SEQUENCE CHARACTERISTICS:
( A ) LENGTH: 14 base pairs
( B ) TYPE: nucleic acid
( C ) STRANDEDNESS: single
( D ) TOPOLOGY: linear ( x i ) SEQUENCE DESCRIPTION: SEQ ID NO:37:

CTGCAGGCCG GTGT 14